Figure 1:
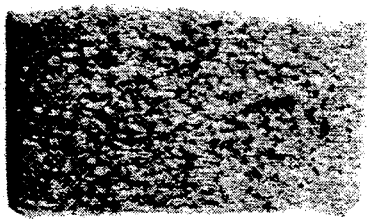

United States Patent [19]

Foresti

[11] Patent Number: 5,292,349
[45] Date of Patent: * Mar. 8, 1994

[54] SURGICAL AID ENDOWED WITH OSTEOTROPIC ACTIVITY

[76] Inventor: Giancarlo Foresti, Via Albricci, 3 - 20122 Milan, Italy

[*] Notice: The portion of the term of this patent subsequent to Jul. 23, 2007 has been disclaimed.

[21] Appl. No.: 309,858

[22] Filed: Feb. 14, 1989

[30] Foreign Application Priority Data

Feb. 16, 1988 [IT] Italy .................................. 19417 A/88

[51] Int. Cl.⁵ .............................................. A61F 2/28
[52] U.S. Cl. ...................................... 623/16; 514/801; 424/423; 106/124
[58] Field of Search ................... 623/16; 424/423, 400, 424/95; 514/801; 106/124

[56] References Cited

U.S. PATENT DOCUMENTS

4,803,075 2/1989 Wallace et al. .................... 424/423

FOREIGN PATENT DOCUMENTS

2756256 6/1979 Fed. Rep. of Germany ... 514/801 X

*Primary Examiner*—Alan W. Cannon
*Attorney, Agent, or Firm*—Venable, Baetjer, Howard & Civiletti

[57] ABSTRACT

The surgical aid endowed with osteotropic activity comprises a base and a suspended substance constituting the active element dispersed in the base. The active element is constituted by granular, ceramic hydroxyapatite, and the base is gelatine of pharmacologic grade in a pure state, to which glycerol is possibly added. The aid is used in anhydrous phase, and as thin sheets and filaments, the flexibility of which increases with increasing percentage of glycerol in the base.

8 Claims, 1 Drawing Sheet

SURGICAL AID ENDOWED WITH OSTEOTROPIC ACTIVITY

The present invention is concerned with a surgical aid performing an osteotropic action.

During the operations of orthopedic surgery, odontiatric surgery, and in parodontium pathology, the need usually occurs for:

filling hollows, removing defects and differences in level of bony planes, reconstructing portions of bony tissue, by operating in such a way as to favour a rapid restoration of the morphology of the bony segment the tissue of which suffered lesions or underwent modifications.

In order to meet the above needs, the use of various types of hydroxy-apatite in presently known.

From an operative viewpoint, the granules of hydroxy-apatite are manually deposited on the region to be treated, so that they may behave as an osteotropic element. Therefore, after healing, the hydroxy-apatite granules are incorporated in a compatible way inside the bony tissue formed.

However, the operation of deposition of the granules of hydroxy-apatite calls for a great skill by the surgeon.

Such a great skill is essential for the surgeon, in order that he can correctly meter the necessary amount of hydroxy-apatite, and to retain it in the area of the lesion in such a way that, after the wound is sutured, the granules of said hydroxy-apatite do not become dispersed during the surgical healing process.

If hydroxy-apatite is not correctly metered, but, for example, a lower than optimum amount thereof is metered, after the healing a satisfactory clinical result is not obtained. If, for example, hydroxy-apatite is metered in a larger amount than as necessary, the healing process ends with a poor clinical result; moreover, the probability is higher that the granules will become dispersed around the bony lesion, therefore causing a waste of a particularly expensive material.

Considerable skill is furthermore required from the surgeon in order that he may correctly insert the granules of hydroxy-apatite inside hollows which are difficult to reach. In doing so, the surgeon may be required to create, by resorting to makeshift means, small instruments or guides, which are capable of fulfilling the surgical requirements.

Particularly difficult situations have to be frequently confronted in the case of odontiatric operations, during which the bony tissue has to be integrated in particularly narrow areas.

The purpose of the present invention is to provide a surgical aid capable of performing an osteotropic action, which obviates the above-said drawbacks.

Such purposes are achieved by a surgical aid endowed with an osteotropic activity, characterized in that it comprises a base and a suspended substance, which constitutes the active element, with said base being constituted by gelatine of pharmacologic grade, in a pure state, and the suspended matter being constituted by ceramic hydroxy-apatite dispersed in the base.

The advantages attained by means of the present invention essentially consist in that:

it can be easily used, in that the metering of the granules of hydroxy-apatite is not required;

it makes it possible to use only the necessary amount with the operation costs being reduced;

it can be easily and stably applied (in that it has a firm structure, not a simply granular structure), without resorting to special equipment;

it is easily anchored in the area in which it is used, with no risk that it may become dispersed or displaced during the clinical healing process;

it is ductile and malleable, so that the product is more readily usable.

Figure 2:
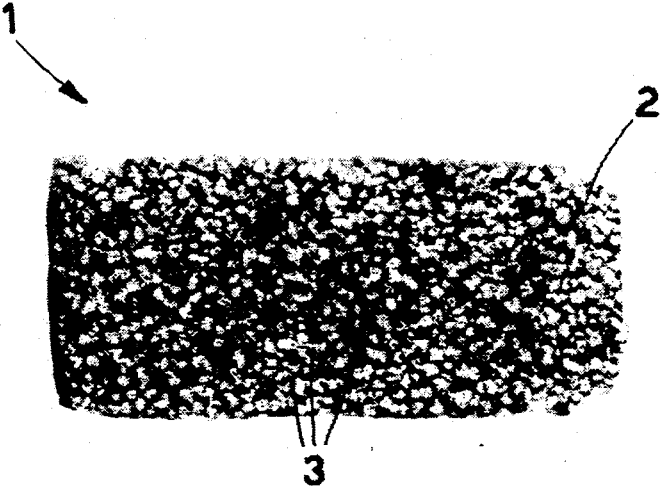

The invention is illustrated for merely exemplifying, and non-limitative, purposes, in the attached drawings, in which FIG. 1 shows a surgical aid according to the present invention, in a form which can be immediately used, in that said surgical aid is given the shape of a laminar structure, with a high density of granules of active material; and FIG. 2 shows a surgical aid according to the present invention, also in a form which can be immediately used, in that said surgical aid is given the shape of a laminar structure with a low density of granules of active material.

Referring to the above cited figures, the surgical aid according to the present invention, generally indicated by the reference numeral 1, comprises a base and a suspended substance, which constitutes the active element. The base 2 is constituted by gelatine of pharmacologic grade, in a pure state (hereinunder simply referred to as the "gel"), and the suspended matter is constituted by granules 3 of ceramic hydroxy-apatite dispersed throughout the base by kneading.

In order to give the product a certain plasticity, glycerol is added.

The optimum chemical composition of the surgical aid in hydrate phase is indicatively as follows:

| | |
|---|---|
| hydroxy-apatite | 61.35% |
| gel | 13.56% |
| glycerol | 12.65% |
| water | 12.44% |

The so-obtained product is dried by evaporation under vacuum, with it being heated to a temperature not higher than 40° C., in order to prevent the gel from undergoing any modifications.

The end product obtained after water evaporation, and therefore of the anhydrous phase, is as follows:

| | |
|---|---|
| hydroxy-apatite | 70.00% |
| gel | 15.05% |
| glycerol | 14.04% |
| water | 0.91% |

The so-obtained product, which is malleable and ductile, is mechanically shaped so as to give it the shape of very thin sheets, small rods, filaments, or any other shapes which make it possible it to be easily and promptly used after being sterilized by means of gamma rays.

The hydroxy-apatite used in order to form the surgical aid is in the form of granules having a diameter within the range of 0.5 to 1.8 mm.

The characteristics of elasticity and flexibility are mainly influenced by the presence of glycerol; more precisely, with increasing glycerol percentage, the characteristics of flexibility and elasticity increase; with the percentages of glycerol gradually decreasing, a substantially more and more rigid product is obtained.

Therefore, a change in glycerol percentage relatively to the gel percentage is provided, which is comprised within the range of about ±4%.

The osteotropic aid shown in FIG. 1 is of the laminar type, with a high granular density, whilst the aid shown in FIG. 2 is of the type with a low granular density.

The application of the aid shown in FIG. 1 is particularly indicated for the reconstruction of bone defects in some parodontium illnesses and the like; whilst the aid shown in FIG. 2 is used after various resections of benign tumors, after the removal of bony tissue owing to traumatic causes, in the substitution of special endoprostheses, and the like. The granules 3 of hydroxy-apatite retained by the base 2 of interstitial gel are visible.

In use, the surgical aid in anhydrous phase is cut into pieces of the required size by means of a common pair of scissors, or suitably dimensioned pre-formed pieces are used.

The gel prevents the granules of hydroxy-apatite 3 from becoming dispersed both during the operation, and during the clinic healing process.

Therefore, the granules of hydroxy-apatite are progressively encapsulated inside the bony tissue during the step of cicatricial rebuilding.

The hydrate gel is progressively dissolved and metabolized.

I claim:

1. A surgical aid endowed with an osteotropic activity, characterized in that it comprises a base and a suspended substance, which constitutes the active element, with said base being constituted by gelatine of pharmacologic grade, in a pure state, and the suspended matter being constituted by ceramic hydroxy-apatite dispersed in the base, said surgical aid containing glycerol and being prepared in two successive phases, said two phases comprising an intermediate hydrate phase and a final anhydrous phase, with said hydrate phase substantially comprising:

| | |
|---|---|
| hydroxy-apatite | 61.35% |
| gelatine | 13.56% |
| glycerol | 12.65% |
| water | 12.44% | and said anhydrous phase substantially comprising:

| | |
|---|---|
| hydroxy-apatite | 70.00% |
| gelatine | 15.05% |
| glycerol | 14.04% |
| water | 0.91%. |

2. A surgical aid according to claim 1, characterized in that the percentage of glycerol is variable relative to the gelatine percentage, by a value of ±4%.

3. A surgical aid according to claim 1, characterized in that hydroxy-apatite is provided as granules, the diameter of which is within the range of 0.5 to 1.8 mm.

4. A surgical aid according to claim 1, characterized in that in the anhydrous state it is both elastic and flexible.

5. A surgical aid endowed with an osteotropic activity, characterized in that it comprises a base and a suspended substance, which constitutes the active element, with said base being constituted by gelatine of pharmacologic grade, in a pure state, and the suspended matter being constituted by ceramic hydroxy-apatite dispersed in the base, said surgical aid containing glycerol and being provided in an anhydrous phase substantially comprising:

| | |
|---|---|
| hydroxy-apatite | 70.00% |
| gelatine | 15.05% |
| glycerol | 14.04% |
| water | 0.91%. |

6. A surgical aid according to claim 5, characterized in that the percentage of glycerol is variable relative to the gelatine percentage, by a value of ±4%.

7. A surgical aid according to claim 5, characterized in that hydroxy-apatite is provided as granules, the diameter of which is within the range of 0.5 to 1.8 mm.

8. A surgical aid according to claim 5, characterized in that in the anhydrous state it is both elastic and flexible.

* * * * *

UNITED STATES PATENT AND TRADEMARK OFFICE
CERTIFICATE OF CORRECTION

PATENT NO. : 5,292,349
DATED : March 8, 1994
INVENTOR(S) : Giancarlo FORESTI It is certified that error appears in the above-identified patent and that said Letters Patent is hereby corrected as shown below:

On the title page of the patent, the [*] Notice should be corrected to read as follows:

The portion of the term of this patent subsequent to April 8, 2008 has been disclaimed.

Signed and Sealed this

Fourth Day of October, 1994

Attest:

BRUCE LEHMAN

*Attesting Officer*         *Commissioner of Patents and Trademarks*